United States Patent [19]
Li

[11] Patent Number: 6,024,974
[45] Date of Patent: Feb. 15, 2000

[54] COMPOSITION AND METHODS FOR TRANSDERMAL DELIVERY OF ACID LABILE DRUGS

[75] Inventor: Chensheng Li, Miami, Fla.

[73] Assignee: Noven Pharmaceuticals, Inc., Miami, Fla.

[21] Appl. No.: 08/863,563

[22] Filed: May 27, 1997

Related U.S. Application Data

[63] Continuation-in-part of application No. 08/369,756, Jan. 6, 1995, abandoned, and a continuation-in-part of application No. PCT/US96/00015, Jan. 11, 1996.

[51] Int. Cl.[7] .................................................. A61F 13/02
[52] U.S. Cl. ........................ 424/448; 424/486; 424/487; 514/946; 514/947; 514/772.5
[58] Field of Search ................... 424/448, 486, 424/487; 514/946, 947, 772.5

[56] References Cited

U.S. PATENT DOCUMENTS

| | | | |
|---|---|---|---|
| 4,537,776 | 8/1985 | Cooper | 514/424 |
| 4,863,970 | 9/1989 | Patel et al. | 514/784 |
| 5,162,315 | 11/1992 | Rajadhyaksha et al. | 514/211 |
| 5,164,190 | 11/1992 | Patel et al. | 424/448 |
| 5,212,199 | 5/1993 | Heiber et al. | 514/415 |
| 5,225,198 | 7/1993 | Sharma et al. | 424/443 |
| 5,252,334 | 10/1993 | Chiang et al. | 424/448 |

FOREIGN PATENT DOCUMENTS

| | | |
|---|---|---|
| 2001618 | 4/1990 | Canada . |
| 2120599 | 5/1993 | Canada . |
| 0 196 769 | 2/1986 | European Pat. Off. . |
| 0 275 716 | 7/1988 | European Pat. Off. . |
| 0 379 045 | 7/1990 | European Pat. Off. . |
| 0 483 105 | 4/1992 | European Pat. Off. . |
| 0 573 133 | 10/1993 | European Pat. Off. . |
| 3836862 A1 | 5/1990 | Germany . |
| 925641 | 10/1986 | Israel . |
| 92/10154 | 6/1992 | WIPO . |
| 93/08795 | 5/1993 | WIPO . |
| 95/18603 | 7/1995 | WIPO . |
| WO 97/03629 | 2/1997 | WIPO . |

OTHER PUBLICATIONS

Aungst et al., "Contributions of Drug solubilization, Partitioning, Barrier Disruption and Solvent Permeation to the Enhancement of Skin Permeation of Various Compounds with fatty Acids and Amines," *Pharmaceutical Research*, vol. 7, No. 7, (1990) p. 712.

Cooper, "Increased Skin Permeability for Lipophilic Molecules," *Journal of Pharmaceutical Sciences*, vol. 73, No. 8 Aug. 1984 p. 1153.

Bialik et al., "The Effects of surfactants on Penetration Across the Skin," *International Journal of Cosmetic Science*, 15: 260–270 (1993).

Eugene Cooper, "Increased Skin Permeability for Lipophilic Molecules", *Journal of Pharmaceutical Sciences*, vol. 73, No. 8, pp. 1153–1156, 1984.

*Primary Examiner*—Jose' G. Dees
*Assistant Examiner*—Michael A. Williamson
*Attorney, Agent, or Firm*—Foley & Lardner

[57] ABSTRACT

A transdermal composition and related method are described. Specifically, the transdermal composition is substantially free of gestodene or substantially free of isopropyl myristate and substantially free of lower alkanols and comprises: (a) a therapeutically effective amount of a pharmacologically active drug which is subject to acid catalyzed degradation; (b) a pharmaceutically acceptable carrier; and (c) a penetration enhancing effective amount of a functional derivative of a fatty acid.

18 Claims, 1 Drawing Sheet

6,024,974

COMPOSITION AND METHODS FOR TRANSDERMAL DELIVERY OF ACID LABILE DRUGS

CROSS REFERENCE TO OTHER APPLICATIONS

This is a continuation-in-part of U.S. patent application Ser. No. 08/369,756, filed Jan. 6, 1995, and abandoned and of PCT/US96/00015, filed Jan. 11, 1996.

FIELD OF THE INVENTION

The present invention relates to compositions and methods for the transdermal delivery of acid labile drugs.

BACKGROUND OF THE INVENTION

The present invention relates generally to a penetration enhancing transdermal composition and related method of use. The penetration enhancer is a functional derivative of a fatty acid. The functional derivative minimizes the acid catalyzed degradation of acid-labile drugs.

Transdermal drug delivery systems are effective means for introducing drugs into the bloodstream by applying them to skin or mucosa. Advantages of transdermal delivery include convenience, comfort, avoidance of the risks associated with enteral and parenteral administration and control over drug absorption. It is particularly suitable for treating conditions which are systemic in nature, and can be used with any drugs that can pass through the skin or mucosa and do not irritate, or cause an allergic reaction at the site of application. Permeability of a drug through the skin may be affected by the stratum corneum, which is characterized by dehydrated and keratinized cells, or by the epidermal layer in the mucosa. The art has recognized that the barriers to the transdermal or percutaneous delivery of drug through the skin can be overcome or reduced by using particular vehicles and carriers into which the drug is incorporated so that the vehicle or carrier can remain at the site of application and increases the drug's penetration at a particular site.

U.S. Pat. No. 4,863,970 by Patel (1989) discloses improved compositions and methods for improving the penetration of a broad category of pharmaceutically-active agents which are lipophilic or hydrophilic, including salts thereof, and which produce little or no skin irritation to human or animal tissue systems. The invention provides penetrating topical compositions based on the use of a pharmaceutically-active agent dissolved in, or admixed with, a penetration-enhancing binary mixture of (a) about 1 to 95% by weight of one or more cell-envelope disordering compounds selected from the group consisting of oleic acid, oleyl alcohol, glycerol monooleate, glycerol dioleate and glycerol trioleate and mixtures thereof and (b) 5–75%, and preferably 5–49%, by weight of a C2 or C3 lower alcohol. In addition, the formulation can optionally contain 0 to 45% by weight of inert ingredients which are soluble within the enhancer composition. Such ingredients can vary from hydrophilic to hydrophobic depending upon the desired combination. Representative inert ingredients include water, polypropylene glycol, polyethylene glycol, polyvinyl alcohols, polyvinylpyrrolidone, mineral oil, silicone oil, ethylene-vinyl acetate polymers or other low molecular weight polymers soluble in water, lower alcohols or suitable oils. This patent does not suggest the particular suitability of functional derivatives of fatty acids in stabilizing drugs subject to acid catalyzed degradation, as well as in functioning as penetration enhancers.

U.S. Pat. No. 5,162,315 describes the use of certain substituted alkanamides as penetration enhancers, but does not suggest their particular suitability with acid labile drugs.

Cooper, E., "Increased Skin Permeability for Lipophilic Molecules" *J. Pharm. Sci.* 73: (Aug. 1984) discloses the use of oleic acid in different concentrations in the presence of propylene glycol as a solid and in the presence of 1,1-butanediol.

Schering AG EPO patent publication No. 573, 133 discloses a combination of gestodene and penetration enhancing agents, generally, including isopropyl myristate.

Although penetration enhancers are well-known in the art, problems associated with combining certain penetration enhancers with certain drugs in transdermal compositions have not been addressed. For instance, applicant has observed that oleic acid, which is a commonly used penetration enhancer, will react with certain drugs, not only causing them to degrade but also creating by-products that interfere with drug penetration and delivery. Applicant has discovered that in order to overcome this type of problem, functional derivatives of fatty acids can be used in transdermal formulations containing drugs that degrade in the presence of weak organic acids, such as oleic acid, particularly over prolonged periods of time, for example, for weeks or months during storage. Such drugs are referred to herein as "acid labile" drugs and include esters, $\alpha$-, $\beta$ unsaturated ketones, 4-aminolevulinic acid, imines and similar compounds subject to degradation in the presence of weak organic acids, especially oleic acid. Applicant was the first to appreciate the above described problem and solution.

The term "fatty acid" is used here in the broadest sense to include saturated and unsaturated, straight and branched chain aliphatic acids having from four to twenty-four carbon atoms. The term "functional derivative" is used here to refer to isosteric modifications of fatty acids or to refer to non-acidic derivatives of the carboxylic functional group of a fatty acid or isosteric modifications thereof.

SUMMARY OF THE INVENTION

The present invention relates to a transdermal composition subtantially free of a lower alkanol and substantially free of gestodene, the composition comprising (a) a therapeutically effective amount of a pharmacologically active drug subject to acid catalyzed degradation; (b) a pharmaceutically acceptable carrier; and (c) a penetration enhancing amount of a functional derivative of a fatty acid.

In another embodiment, the present invention relates to a transdermal composition subtantially free of a lower alkanol and substantially free of isopropyl myristate, the composition comprising (a) a therapeutically effective amount of a pharmacologically active drug subject to acid catalyzed degradation; (b) a pharmaceutically acceptable carrier; and (c) a penetration enhancing amount of a functional derivative of a fatty acid.

In another embodiment, the present invention relates to a method of delivering a pharmacologically active drug comprising topically applying to a mammal a composition comprising (a) a therapeutically effective amount of a pharmacologically active drug which is subject to acid catalyzed degradation; (b) a pharmaceutically acceptable carrier; and (c) a penetration enhancing effective amount of a functional derivative of a fatty acid.

The preparation is substantially free of any lower alkanols, i.e., lower molecular weight alkanols, i.e., those containing 1 to 3 carbon atoms. "Substantially free" means that the composition contains less than 3 percent and more preferrably less than 1 percent of the ingredient in question.

In one embodiment, the composition also is substantially free of gestodene. In another embodiment, the composition is substantially free of isopropyl myristate.

DETAILED DESCRIPTION OF THE PREFERRED EMBODIMENTS

Figure 1:
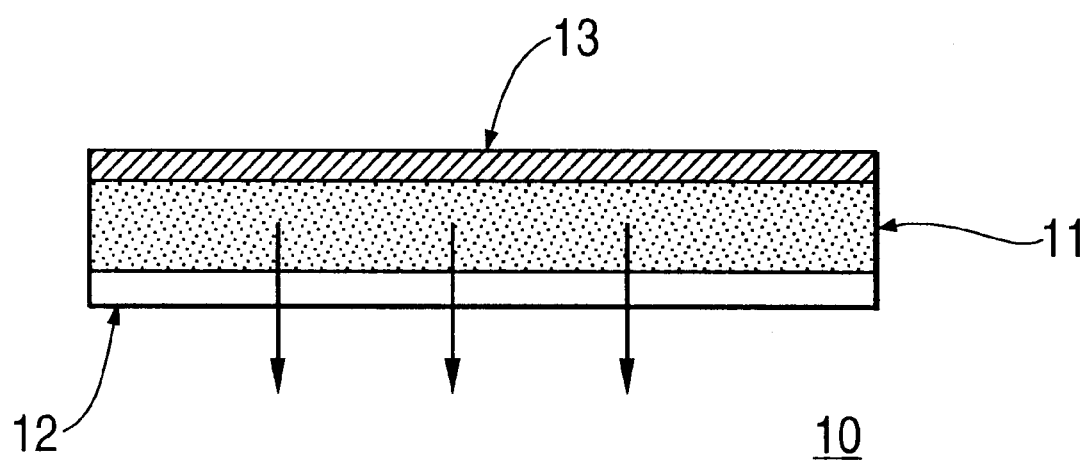
FIG. 1 shows a schematic illustration of an adhesive monolithic device, in accordance with the present invention.

The present invention provides a penetration enhancing transdermal composition comprising (a) a therapeutically effective amount of a pharmacologically active drug which is subject to acid catalyzed degradation; (b) a pharmaceutically acceptable carrier; and (c) a penetration enhancing effective amount of a functional derivative of a fatty acid.

The term "functional derivative of a fatty acid" means isosteric modifications of fatty acids or non-acidic derivatives of the carboxylic functional group of a fatty acid or isosteric modifications thereof. Specifically, a functional derivative of a fatty acid includes a saturated, or preferably unsaturated, aliphatic acid in which the —COOH group is substituted with a functional derivative thereof, such as an alcohol, —CH$_2$OH, polyols, OH—CH—OH, amides, —CONH$_2$, and substituted derivatives thereof, including esters, ethers and N,N' disubstituted amides. The term "fatty acid" as used here and as noted above means higher molecular weight, straight and branched chain saturated and unsaturated aliphatic acids of four to twenty-four carbons, including but not limited to those having an even number of carbon atoms derived from animals and plants. The functional derivative of a fatty acid is intended to include at least one functional derivative of a fatty acid.

As used herein, the term "pharmacologically active drug" and its equivalents, "agent," "bioactive agent," and "medicament," are intended to have the broadest meaning and includes at least one of any therapeutically, prophylactically and/or pharmacologically or physiologically beneficial active substance, or mixture thereof, which is delivered to a living organism to produce a desired, usually beneficial, effect.

More specifically, any drug which is capable of producing a pharmacological response, localized or systemic, irrespective of whether therapeutic, diagnostic, or prophylactic in nature, particularly in animals, is within the contemplation of the invention. It should be noted that the drugs and/or bioactive agents may be used singularly or as a mixture of two or more such agents, and in amounts sufficient to prevent, cure, diagnose or treat a disease or other condition, as the case may be.

However, the drugs for use in this invention are those which are acid labile, namely those which are degraded by acids, even organic acids, or are degraded in acid catalyzed reactions. The invention is particularly suitable for use with α, β unsaturated ketones, especially 3-oxo-4, 5 dehydrosteroids, esters, and α-ketoamino acids and imines. Preferably the drug of the present invention is norethindrone acetate. Other drugs which may be included are:

ANABOLIC STEROIDS such as Androisoxazole, Bolasterone, Clostebol, Ethylestrenol, Formyldienolone, 4-Hydroxy-19-nortestosterone, Methenolone, Methyltrienolone, Nandrolone, Nandrolone Decanoate, Nandrolone p-Hexyloxyphenyl-propionate, Nandrolone Phenpropionate, Norbolethone, Oxymesterone, Quinbolone, Stenbolone, Trenbolone ANDROGENIC STEROIDS such as Boldenone, Fluoxymesterone, Mestanolone, Mesterolone, Methandrostenolone, 17-Methyltestosterone, 17α-Methyl-testosterone 3-Cyclopentyl Enol Ether, Norethandrolone, Normethandrone, Oxandrolone, Oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Phenylacetate, Testosterone Propionate, Tiomesterone DIURETIC STEROIDS such as Canrenone, Oleandrin, Spironolactone, and PROGESTOGENS such as Anagestone, Chlormadinone Acetate, Delmadinone Acetate, Demegestone, Dimethisterone, Dydrogesterone, Ethinylestrenol, Ethisterone, Ethynodiol, Ethynodiol Diacetate, Flurogestone Acetate, Gestodene, Gestonorone Caproate, Haloprogesterone, 17-Hydroxy-16-methylene-progesterone, 17α-Hydroxyprogesterone, 17α-Hydroxyprogesterone Caproate, Medrogestone, Medroxyprogesterone, Megestrol Acetate, Melengestrol, Norethindrone, Norethindrone Acetate, Norethynodrel, Norgesterone, Norgestimate, Norgestrel, Norgestrienone, 19-Norprogesterone, Norvinisterone, Pentagestrone, Progesterone, Promegestone, Quingestrone, Trengestone The above list of pharmaceutical agents is based upon the list provided in *The Merck Index,* 11th Edition, Merck & Co. Rahway, N.J. (1989).

The drugs and mixtures thereof can be present in the composition of the present invention in different forms, depending on which form yields the optimum delivery characteristics. Thus, the drug, containing acidic or basic groups, respectively, can be in free acid or base form, or in the form of salts, esters, or any other pharmacologically acceptable functional derivatives, including components of molecular complexes.

The amount of drug to be incorporated in the composition varies depending on the particular drug, the desired therapeutic effect, and the time span for which the device is to provide therapy. The drug is used in a "pharmacologically effective amount." This means that the concentration of the drug is such that in the composition it results in a therapeutic level of drug delivered over the term that the transdermal dosage form is to be used, preferably with zero order kinetics. Such delivery is dependent on a great number of variables including the drug, the form of drug, the time period for which the individual dosage unit is to be used, the flux rate of the drug from the system and a number of other variables. The amount of drug needed can be experimentally determined based on the flux rate of the drug through the system and through the skin when used with and without enhancers. Having determined the flux rate needed, the transdermal delivery system is designed so that the release rate over the period of time of therapeutic use will be at least equal to the flux rate. Of course, the surface area of the transdermal delivery system also affects the delivery of the drug from the system.

In general, therapeutic amounts of drug can be delivered from the composition containing 0.05% to about 50% by weight of drug, or more preferably from about 0.1% to about 30% by weight. However, the composition of this invention is particularly useful for drugs which are used in relatively low concentrations, especially 0.1% to 20% of the total composition.

The carrier of the present invention can be at least one of any pharmaceutically acceptable carrier which is capable of conforming to a surface with which it comes into contact and capable of maintaining the contact so as to facilitate topical application without any adverse physiological response, and which maintain their form and do not appreciably decompose in use. Such carriers can be, among other things, creams, ointments, oils, lubricants and adhesives. In the preferred embodiment, the carrier is an adhesive or combinations of adhesives such as any of the non-toxic polymers, particularly those known in the art to carry drugs for transdermal delivery, including natural or synthetic elastomers, such as polyisobutylene, styrene, butadiene, styrene isoprene block copolymers, acrylics, urethanes, silicones, styrene butadiene copolymers, acrylic acid polymers, polyacrylates, and polysaccharides such as karaya gum, tragacanth gum, pectin, guar gum, cellulose, and cellulose derivative such as methyl cellulose, propyl cellulose, cellulose acetate and the like, along with other substances capable of forming a solid colloid that can adhere to the skin or mucosa, alone or in combination with other carriers. The term "adhesive" means a substance, inorganic or organic, natural or synthetic that is capable of surface attachment at the intended application site.

In the most preferred embodiment, the carrier of the present invention is a pressure sensitive adhesive, i.e. a viscoelastic material which adheres instantaneously to most substrates with the application of very slight pressure and remains permanently tacky. Preferably, the pressure sensitive adhesive comprises a blend of at least two polymers and a soluble polyvinylpyrrolidone ("PVP").

The soluble PVP is preferably used in an amount effective to solubilize the drug.

A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB) of different molecular weights, the resultant mixtures being a pressure-sensitive adhesive. In the last case, the polymers of lower molecular weight in the mixture are not considered to be "tackifiers," said term being reserved for additives which differ other than in molecular weight from the polymers to which they are added.

As used herein, the term "rubber" refers to a viscoelastic material which has the properties of a pressure-sensitive adhesive and which contains at least one natural or synthetic elastomeric polymer. Suitable rubbers include polysiloxane, polyisobutylene and natural rubber.

The multiple polymer adhesive system is preferably formulated so that it is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In general, the multiple polymer adhesive system should have a glass transition temperature ($T_\beta$), measured using a differential scanning calorimeter, of between about −70° C. and 0° C.

The term "acrylic polymer" is used herein as in the art interchangeably with polyacrylate, polyacrylic and acrylic adhesive. The acrylic-based polymer and silicone-based polymer are preferably in a ratio by weight, respectively, from about 2:98 to about 96:4, more preferably from about 2:98 to about 90:10, and even more preferably about 2:98 to about 86:14.

Suitable acrylic adhesives are commercially available and include the polyacrylate adhesives sold under the trademarks Duro-Tak 80-1194, 80-1196, 80-1197, 2287, 2516 and 2852 by National Starch and Chemical Corporation, Bridgewater, N.J. Other suitable acrylic adhesives are those sold under the trademarks Gelva-Multipolymer Solution GMS 737, 788, 1151 and 1430 (Monsanto; St. Louis, Mo.).

The rubber adhesives useful in practicing the invention include hydrocarbon polymers such as natural and synthetic polyisoprene, polybutylene and polyisobutylene, styrene/butadiene polymers, styrene-isoprene-styrene block copolymers, hydrocarbon polymers such as butyl rubber, halogen-containing polymers such as polyacrylo-nitrile, polytetrafluoroethylene, polyvinylchloride, polyvinylidene chloride, and polychloropene, and polysiloxanes and other copolymers thereof.

Suitable polysiloxanes include silicone pressure-sensitive adhesives which are based on two major components: a polymer, or elastomer, and a tackifying resin. The polysiloxane adhesive is usually prepared by cross-linking the elastomer, typically a high molecular weight polydiorganosiloxane, with the resin, to produce a three-dimensional siloxane structure, via a condensation reaction in an appropriate organic solvent. The ratio of resin to elastomer is the most important factor which can be adjusted in order to modify the physical properties of polysiloxane adhesives. Sobieski, et al., "Silicone Pressure Sensitive Adhesives," *Handbook of Pressure-Sensitive Adhesive Technology*, 2nd ed., pp. 508–517 (D. Satas, ed.), Van Nostrand Reinhold, New York (1989).

Suitable silicone pressure-sensitive adhesives are commercially available and include the silicone adhesives sold under the trademarks BIO-PSA X7-4201 methylated trimethylated silica in heptane X7-4203 (methylated trimethylate silica in toluene) Q7-4503 (trimethylated silica treatment with dimethyl siloxane, in toluene, as describe at Chemical Abstract Registry No. 068440700), X7-4603 (trimethylated silica treated with dimethyl siloxane, in toluene, as described at Chemical Abstract registry No. 068440700), X7-4301 ), (methylated trimethylated silica in heptane), X7-4303 (methylated trimethylated silica in toluene), X7-4501, (trimethylated silica treated with dimethyl siloxane, in heptane as described at Chemical Abstract Registry No. 068440700), and by Dow Corning Corporation, Medical Products, Midland, Mich. BIO-PSA X7-4203, X7-4301 and X7-4303 are particularly suitable for use in formulations containing amine-functional drugs, such as albuterol.

In the practice of preferred embodiments of the invention, the polysiloxane constitutes preferably from about 9% to about 97% of the total weight of the pressure-sensitive adhesive composition, more preferably about 12% to about 97%, and optimally about 14% to about 94%.

The composition of the present invention may also include a drug solubilizing amount of a solvent. A "drug solubilizing effective amount of a solvent" refers to non-toxic, pharmaceutically acceptable substances, preferably liquids which do not substantially negatively affect the adhesion properties of the system and in which the drugs in the amounts employed are fully soluble. For instance, the solvent may be primarily a polyhydric alcohol or combination of polyhydric alcohols, particularly if the carrier is a gum. The term polyhydric alcohol means any organic polyol. Polyhydric alcohols include glycols, triols and polyols having 4 to 6 alcoholic hydroxyl groups.

In a preferred embodiment, the carrier is a pressure sensitive adhesive comprising a blend of polymers including PVP. Indeed, soluble PVP has been found to be highly effective in solubilization of drugs in adhesive-type transdermal drug delivery systems according to the invention, wherein the carrier is a blend of polymers. In particular, soluble PVP has proved useful in maintaining a norethindrone acetate (NETA) system and an NETA/estradiol system substantially crystal-free. Other specific drugs for which soluble PVP is particularly usefully employed according to the invention include albuterol, estradiol, haloperidol and alprazolam.

The amount and type of soluble PVP required in the foregoing preferred embodiment will depend on the quantity and type of drug present in the adhesive, as well as the type of adhesive.

However, for drug molecules which are not readily soluble in the polymer system containing PVP, another solvent or "co-solvent" for the drug and polymer can be added. Co-solvents, such as lecithin, retinol derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the drug in the multiple polymer adhesive system.

In a preferred embodiment of the invention, a transdermal drug delivery system is prepared by mixing a soluble PVP, polyacrylate, polysiloxane, drug, co-solvent(s), and tackifying agent, if needed, in an appropriate volatile solvent(s), then casting the mixture and removing the solvent(s) by evaporation to form a film. Thus, the composition is substantially free of the volatile solvents, e.g. an alkanol.

Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer.

According to the present invention, a "penetration enhancing amount" is an amount up to about 20% by weight of the whole composition, but preferably an amount of about 1% to about 10% by weight.

The penetration enhancer of the present invention is a functional derivative of a fatty acid, which includes isosteric modifications of fatty acids or non-acidic derivatives of the carboxylic functional group of a fatty acid or isosteric modifications thereof. Preferably, the functional derivative of a fatty acid is an unsaturated alkanoic acid in which the —COOH group is substituted with a functional derivative thereof, such as alcohols, polyols, amides and substituted derivatives thereof, including esters, ethers and N,N' disubstituted amides. The term "fatty acid" means a fatty acid that has four to twenty-four carbon atoms, and includes but is not limited to those derived from animals and plants. Particular preferred derivatives are those based on oleic acid, e.g., oleyl alcohol, as follows:

| Group | Formulation | CFTA Name |
|---|---|---|
| ALCOHOLS | $CH_3(CH_2)_7CH=CH(CH_2)_8OH$ | Oleyl Alcohol |
|  | $CH_3(CH_2)_7CH=CH(CH_2)_7CH_2(OCH_2CH_2)_2OH$ | Oleith-2 |
|  | $CH_3(CH_2)_7CH=CH(CH_2)_7CH_2(OCH_2CH_2)_5OH$ | Oleith-5 |
|  | $CH_3(CH_2)_7CH=CH(CH_2)_7CH_2(OCH_2CH_2)_{10}OH$ | Oleith-10 |
|  | $CH_3(CH_2)_7CH=CH(CH_2)_7CH_2(OCH_2CH_2)_{20}OH$ | Oleith-20 |
|  | $CH_3(CH_2)_7CH=CH(CH_2)_7CH_2(OCH_2CH_2)_{30}OH$ | Oleith-30 |
|  | $CH_3(CH_2)_7CH=CH(CH_2)_7CH_2(OCH\text{—}CH_2)_{10}OH$ with $CH_3$ | PPG-10 Oleyl Ether |
|  | $CH_3(CH_2)_7CH=CH(CH_2)_7CH_2(OCH\text{—}CH_2)_{20}OH$ with $CH_3$ | PPG-20 Oleyl Ether |
|  | $CH_3(CH_2)_7CH=CH(CH_2)_7CH_2(OCH\text{—}CH_2)_{50}OH$ with $CH_3$ | PPG-50 Oleyl Ether |
| ESTERS | $CH_3(CH_2)_7CH=CH(CH_2)_7C(=O)\text{—}OCH_2CHOHCH_2OH$ | Glyceryl Oleate |
| AMIDES | $CH_3(CH_2)_7CH=CH(CH_2)_7C(=O)\text{—}NH_2$ | Oleamide |
|  | $CH_3(CH_2)_7CH=CH(CH_2)_7C(=O)\text{—}N(CH_2CH_2OH)_2$ | Oleamide DEA |
|  | $CH_3(CH_2)_7CH=CH(CH_2)_7C(=O)\text{—}NH\text{—}CH_2CH_2OH$ | Oleamide MEA |

-continued

| Group | Formulation | CFTA Name |
|---|---|---|
| | CH$_3$(CH$_2$)$_7$CH=CH(CH$_2$)$_7$C(O)—NH—CH$_2$CH(CH$_3$)—OH | Oleamide MIPA |
| ZWITTERION | CH$_3$(CH$_2$)$_7$CH=CH(CH$_2$)$_7$CH—N$^+$(CH$_3$)(CH$_3$)—CH$_2$COO$^-$ | Oleyl Betamine |

In the preferred embodiment of the present invention, wherein the carrier is a pressure sensitive adhesive comprising a blend of polymers, an exemplary general method of preparation is as follows:

1. Appropriate amounts of soluble PVP, solvent(s), functional derivative of a fatty acid enhancer(s), and organic solvent(s) (for example toluene) are combined and thoroughly mixed together in a vessel.

2. The drug is then added to the mixture and agitation is carried out until the drug is uniformly mixed in.

3. Appropriate amounts of polysiloxane and polyacrylate are then added to the drug mixture, and thoroughly mixed.

4. The formulation is then transferred to a coating operation where it is coated onto a protective release liner at a controlled specified thickness. The coated product is then passed through an oven in order to drive off all volatile processing solvents.

5. The dried product on the release liner is then joined to the backing material and wound into rolls for storage.

6. Appropriate size and shape "systems" are die-cut from the roll material and then pouched.

The order of steps, the amount of the ingredients, and the amount and time of agitation or mixing may be important process variables which will depend on the specific polymers, drug, cosolvents, and enhancers used in the formulation. These factors can be adjusted by those skilled in the art, while keeping in mind the object of providing a uniform product. It is believed that a number of other methods, including changing some of the order of steps, can be carried out and will give desirable results. In addition to having various shapes, the dosage units produces may come in various sizes. A surface area in the range of 1 to 200 square centimeters is contemplated, and the presently preferred sizes are: 5, 10, 15, 20, 30, 30 and 60 square centimeters.

The preparation is substantially free of any lower alkanols, i.e., lower molecular weight alkanols, e.g. those containing 1 to 3 carbon atoms. "substantially free" means that the composition contains less than 3 percent and more preferably less than 1 percent of the ingredient in question. The preparation may also be substantially free of gestodene and may be substantially free of isopropyl myristate.

To summarize, the preferred and optimum compositions for rubber and polyacrylate embodiments are as follows:

TABLE I

PERCENT BY WEIGHT

| Component | Preferred Range | Optimum Range |
|---|---|---|
| Rubber | 97–9 | 94–14 |
| Polyacrylate | 0–95 | 5–85 |
| PVP | 0–20 | 5–15 |
| Co-solvent (s) | 0–30 | 0–20 |
| Fatty acid derivative Enhancer | 1–20 | 5–15 |
| Drug(s) | 0.05–50 | 0.1–20 |

In certain embodiments of the invention a plasticizer or tackifying agent is incorporated into the formulation to improve the adhesive characteristics of the pressure-sensitive adhesive composition.

The compositions of this invention may further be provided with various thickeners, fillers and other additives known for use with transdermal drug delivery systems. Where the composition tends to absorb water, for example, when lecithin is used as a co-solvent, hydrophilic substances are especially useful.

In a device aspect of the invention, the pressure-sensitive adhesive composition can be used as an adhesive portion of any transdermal drug delivery system (e.g., a reservoir device) or it can comprise an adhesive monolithic device. Of course, the principles of the invention would still apply to embodiments where the transdermal drug delivery composition is not a pressure-sensitive adhesive and comprises a drug reservoir.

Reference to FIG. 1 shows a schematic illustration of an adhesive monolithic device embodiment of the invention 10. The transdermal drug delivery system comprises a monolithic body 11 of a defined geometric shape with a protective release liner 12 on one side of monolithic body 11 and a backing layer 13 on the other side. Removal of the release liner 12 exposes the pressure-sensitive multiple polymer adhesive composition which functions as the drug carrier matrix, a drug penetration enhancer and as the means of applying the system to the patient.

A device, or individual dosage unit, of the present invention can be produced in any manner known to those of skill in the art. After the dermal composition is formed, it may be brought into contact with the backing layer in any manner known to those of skill in the art. Such techniques include calendar coating, hot melt coating, solution coating, etc. Of course, backing materials are well known in the art and can comprise plastic films of polyethylene, vinyl acetate resins, polyester, polypropylene, BAREX®, ethylene/vinyl acetate copolymers, polyvinyl chloride, polyurethane, and the like, metal foils, non-woven fabric, cloth, coextrusions or laminations of the above and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art.

The configuration of the transdermal delivery system of the present invention can be in any shape or size as is necessary or desirable. Illustratively, a single dosage unit may have a surface area in the range of 1 to 200 cm$^2$. Preferred sizes are from 5 to 60 cm$^2$.

In yet another embodiment, the present invention relates to a method of enhancing the penetration of a pharmacologically active drug in a transdermal composition comprising topically applying to a mammal a transdermal composition comprising (a) a therapeutically effective amount of a pharmacologically active drug; (b) a pharmaceutically acceptable carrier; and (c) a penetration enhancing effective amount of a derivative of a fatty acid.

"Enhancing penetration" refers to the acceleration of a drug through the skin or mucosa. "Topical application" means the administration of the composition of the invention to a mammal in any way which results in the physical contact of the composition with skin or mucosa at an anatomical site of interest. Those of skill in the art would know what dosages and length of use to prescribe for a given formulation, depending upon the desired therapeutic result, the type of drug and other components in the transdermal composition, the size of the transdermal composition in its final form and the age and physical state of the mammal.

The following specific examples are included as illustrative of pressure-sensitive adhesive compositions and transdermal drug delivery systems, and methods of making same, within the contemplation of the invention. These examples are in no way intended to be limiting of the scope of the invention.

EXAMPLE 1

| COMPONENT | PERCENT BY WEIGHT |
| --- | --- |
| Polysiloxane A Adhesive (BIO-PSA Q7-4503) | 5.0 |
| Polysiloxane B Adhesive (BIO-PSA X7-4603) | 71.6 |
| Polyacrylate Adhesive (GMS 737) | 5.0 |
| Oleamide | 6.0 |
| Dipropylene Glycol | 2.0 |
| Polyvinylpyrrolidone (Kollidon 30) | 5.0 |
| Polyoxyethylene (2) Oleyl Ether (Brij 93) | 2.0 |
| Norethindrone Acetate | 3.0 |
| Estradiol | 0.4 |
|  | 100.0 |

EXAMPLE 2

| COMPONENT | PERCENT BY WEIGHT |
| --- | --- |
| Polysiloxane A Adhesive (BIO-PSA Q7-4503) | 5.0 |
| Polysiloxane B Adhesive (BIO-PSA X7-4603) | 71.6 |
| Polyacrylate Adhesive (GMS 737) | 5.0 |
| Oleamide | 6.0 |
| Dipropylene Glycol | 4.0 |
| Polyvinylpyrrolidone (Kollidon 30) | 5.0 |
| Norethindrone Acetate | 3.0 |
| Estradiol | 0.4 |
|  | 100.0 |

EXAMPLE 3

An estradiol/norethindrone acetate-polymer mixture is prepared by combining 0.8 parts of estradiol, 3.0 parts of norethindrone acetate, 4.0 parts of polyoxyethylene (2) oleyl ether (Brij 93), 6.0 parts of oleyl alcohol, 10.0 parts of polyvinylpyrrolidone (Kollidon Va. 64), 5.0 parts of polyacrylate adhesive (GMS 737), and 71.2 parts of polysiloxane adhesive (BIO-PSA X7-4603) in an appropriate container, and mixing well until the mixture is completely homogeneous. The resulting composition has the ingredient concentrations on a "dry" basis, that is, after removal of volatile process solvents, given below.

| COMPONENT | PERCENT BY WEIGHT |
| --- | --- |
| Polysiloxane Adhesive (BIO-PSA Q7-4603) | 71.2 |
| Polyacrylate Adhesive (GMS 737) | 5.0 |
| Oleyl Alcohol | 6.0 |
| Polyoxyethylene (2) Oleyl Ether (Brij 93) | 4.0 |
| Polyvinylpyrrolidone (Kollidon VA 64) | 10.0 |
| Norethindrone Acetate | 3.0 |
| Estradiol | 0.8 |
|  | 100.0 |

EXAMPLE 4

| COMPONENT | PERCENT BY WEIGHT |
| --- | --- |
| Acrylic Adhesive (Dura-Tak 87-2097) | 73.0 |
| Silicone Adhesive (BIO-PSA X7-4303) | 12.0 |
| Oleyl Alcohol | 6.0 |
| Dipropylene Glycol | 4.0 |
| Scopolamine | 5.0 |
|  | 100.0 |

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A transdermal composition substantially free of weak organic acids, of lower alkanols and of gestodene, the composition comprising (a) a therapeutically effective amount of a pharmacologically active drug subject to acid catalyzed degradation; (b) a pharmaceutically acceptable carrier; and (c) a penetration enhancing amount of a functional derivative of a fatty acid, wherein said derivative is selected from the group consisting of amides, alcohols, and polyols.

2. The composition of claim 1, wherein said derivative is selected from the group consisting of oleamide and oleyl alcohol.

3. The composition of claim 2, wherein said drug is norethindrone acetate.

4. The composition of claim 3, wherein said carrier is a pressure sensitive adhesive.

5. The composition of claim 1, which further comprises a solvent.

6. The composition of claim 5, wherein said carrier is comprised of a polyacrylate, said drug is norethindrone acetate; said penetration enhancer is selected from the group consisting of oleyl alcohol and oleamide; and said solvent is a glycol.

7. The composition of claim 5, comprising:

3% by weight of the total composition of norethindrone acetate; 0.4 percent by weight of the total composition of estradiol; 5.0 percent by weight of the total composition of polysiloxane adhesive comprising trimethylated silica treated with dimethyl siloxane in toluene; 71.6 percent by weight of the total composition of polysiloxane adhesive comprising trimethylated silica treated with polydimethylsiloxane in toluene; 5.0 percent by weight of the total composition of polyacrylate adhesive; 6.0 percent by weight of the total composition of oleamide; 2.0 percent by weight of the total composition of dipropylene glycol; 5.0 percent by weight of the total composition of polyvinylpyrrolidone; and 2.0 percent by weight of the total composition of polyoxyethylene (2) oleyl ether.

8. The composition of claim 5, comprising:

3% by weight of the total composition of norethindrone acetate; 0.4 percent by weight of the total composition of estradiol; 5.0 percent by weight of the total composition of polysiloxane adhesive comprising trimethylated silica treated with dimethyl siloxane in toluene; 71.6 percent by weight of the total composition of polysiloxane adhesive comprising trimethylated silica treated with polydimethylsiloxane in toluene; 5.0 percent by weight of the total composition of polyacrylate adhesive; 6.0 percent by weight of the total composition of oleamide; 4.0 percent by weight of the total composition of dipropylene glycol; and 5.0 percent by weight of the total composition of polyvinylpyrrolidone.

9. The composition of claim 5, comprising:

3% by weight of the total composition of norethindrone acetate; 0.8 percent by weight of the total composition of estradiol; 71.2 percent by weight of the total composition of polysiloxane adhesive comprising trimethylated silica treated with dimethyl siloxane in toluene; 5.0 percent by weight of the total composition of polyacrylate adhesive; 6.0 percent by weight of the total composition of oleyl alcohol; 4.0 percent by weight of the total composition of polyoxyethylene (2) oleyl ether; and 10.0 percent by weight of the total composition of polyvinyl-pyrrolidone.

10. The transdermal composition of claim 1, wherein said drug is scopolomine.

11. A method of enhancing the penetration of a pharmacologically active drug comprising topically applying to a mammal a composition comprising: (a) a therapeutically effective amount of a pharmacologically active drug which is subject to acid catalyzed degradation; (b) a pharmaceutically acceptable carrier; and (c) a penetration enhancing effective amount of a functional derivative of a fatty acid, wherein said derivative is selected from the group consisting of amides, alcohols, and polyols, and wherein said composition is substantially free of weak organic acids, of lower alkanols, and of gestodene.

12. The method of claim 11, wherein said drug is scopolomine.

13. A stabilized patch device for transdermal delivery of a steroid drug containing a 3-keto-4-en functional group, wherein said steroid drug is stable upon extended storage of said device, comprising an effective amount of said steroid drug and a carrier, wherein said carrier has no acid functional groups and forms no acid functional groups upon storage, and wherein said carrier is substantially free of weak organic acids, of lower alkanols, and of gestodene.

14. The stabilized patch device of claim 13, wherein said steroid drug is selected from the group consisting of sex hormones and corticosteroids.

15. The stabilized patch device of claim 14, wherein said device is a matrix patch wherein said carrier comprises a biocompatible polymeric adhesive with which said steroid drug is intimately admixed.

16. The stabilized patch device of claim 15, wherein said steroid drug is a sex hormone selected from the gourp consisting of progestins, androgens, and mixtures thereof.

17. The stabilized patch device of claim 16, wherein said sex hormone is a progestin and said progestin is a member selected from the group consisting of progesterone, ethisterone (17α-ethinyltestosterone), medroxyprogesterone, hydroxyprogesterone, norethindrone (17α-ethinyl-19-nortestosteron), norethindrone acetate (17α-ethinyl-19-nortestosterone acetate), dydrogesterone (9β, 10α-pregna-4, 6-diene-3, 20-dione), chlomadinone acetate (6-chloro-6-dehydro-17α-acetoxyprogesterone), norgestrel (13β-ethyl-17α-ethinyl-17β-hudroxygon-4-en-3-one, and esters and mixtures thereof.

18. The stabilized patch device of calim 17, wherein said progestin is norethindrone acetate.

\* \* \* \* \*